United States Patent [19]

Sih

[11] 4,296,246
[45] Oct. 20, 1981

[54] 13,14-DIDEHYDRO-11-DEOXY-11-HYDROXYMETHYL-19-OXO-PGF$_1$ COMPOUNDS

[75] Inventor: John C. Sih, Kalamazoo, Mich.

[73] Assignee: The Upjohn Company, Kalamazoo, Mich.

[21] Appl. No.: 131,970

[22] Filed: Mar. 20, 1980

Related U.S. Application Data

[62] Division of Ser. No. 25,879, Apr. 2, 1979.

[51] Int. Cl.$^3$ ............................................. C07C 177/00
[52] U.S. Cl. .................................... 562/503; 560/121; 260/404; 260/404.5; 260/408; 260/410; 260/410.5; 260/410.9 R

[58] Field of Search ......................... 560/121; 502/503; 260/404, 404.5, 408, 410, 410.5, 410.9 R, 413

[56] References Cited

U.S. PATENT DOCUMENTS 4,054,575 10/1977 Marx et al. ........................... 560/121

Primary Examiner—Robert Gersil
Attorney, Agent, or Firm—Robert A. Armitage

[57] ABSTRACT

The present invention provides novel 13,14-didehydro-11-deoxy-11-hydroxymethyl-19-oxo-PGF$_1$ compounds, which are useful for a variety of pharmacological purposes, e.g., antiasthmatic indications.

4 Claims, No Drawings

13,14-DIDEHYDRO-11-DEOXY-11-HYDROXYMETHYL-19-OXO-PGF₁ COMPOUNDS

CROSS REFERENCE TO RELATED APPLICATION

This application is a division of Ser. No. 025,879, filed Apr. 2, 1979.

DESCRIPTION

1. Background of the Invention

The present invention relates to novel prostaglandin analogs. Particularly, the invention relates to prostaglandin analogs wherein the C-19 position is substituted by oxo, i.e., 19-keto-PG compounds or 19-oxo-PG compounds. Most particularly, the present invention relates to novel 13,14-Didehydro-11-deoxy-11-hydroxymethyl-19-oxo-PGF₁ compounds, a disclosure of the preparation and pharmacological use of which is incorporated here by reference from U.S. Serial No. 025,899, filed Apr. 2, 1979.

2. Prior Art

Prostaglandins exhibiting a variety of substitution at the C-19 position are known. See particularly J. C. Sih, et al., JACS 91:3685 (1969) wherein 19-oxo-PGE₂ and 13,14-dihydro-19-oxo-PGE₁ are disclosed. Further, Chemical Abstracts 86:43265H purportedly discloses 19-oxo-PGF₂α. The abstract is derived from Japanese Kokai 76 82,245.

SUMMARY OF THE INVENTION

The present invention particularly provides: a compound of the formula

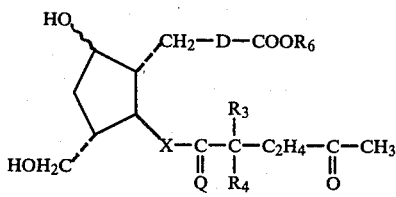

wherein D is
(1) $(CH_2)_3-(CH_2)_g-CH_2-$, or
(2) $(CH_2)_3-(CH_2)_g-CF_2-$;
wherein g is zero, one, two, or three;
wherein Q is α-OH:β-R₅ or α-R₅:β-OH, wherein R₅ is hydrogen or methyl;
wherein R₆ is
  (a) hydrogen,
  (b) alkyl of one to 12 carbon atoms, inclusive,
  (c) cycloalkyl of 3 to 10 carbon atoms, inclusive,
  (d) aralkyl of 7 to 12 carbon atoms, inclusive,
  (e) phenyl,
  (f) phenyl substituted with one, 2, or 3 chloro or alkyl groups of one to 3 carbon atoms, inclusive,
  (g) $-(p-Ph)-CO-CH_3$,
  (h) $-(p-Ph)-NH-CO-(p-Ph)-NH-CO-CH_3$,
  (i) $-(p-Ph)-NH-CO-(p-Ph)$,
  (j) $-(p-Ph)-NH-CO-CH_3$,
  (k) $-(p-Ph)-NH-CO-NH_2$,
  (l) $-(p-Ph)-CH=N-NH-CO-NH_2$,
  (m) β-naphthyl,
  (n) $-CH_2-CO-R_{28}$,
wherein (p-Ph) is para-phenyl or inter-para-phenylene,
wherein R₂₈ is phenyl, p-bromophenyl, p-biphenylyl, p-nitrophenyl, p-benzamidophenyl, or 2-naphthyl, or
  (o) a pharmacologically acceptable cation;
wherein R₃ and R₄ are hydrogen, methyl, or fluoro, being the same or different, with the proviso that one of R₃ and R₄ is fluoro only when the other is hydrogen or fluoro; and
wherein X is $-C\equiv C-$.

The compounds of the present invention are particularly useful for inducing prostaglandin-like biological effects, as described in U.S. Ser. No. 026,066. Uses of compounds in accordance with the present invention include, therefore, antiasthmatic indications.

DESCRIPTION OF THE PREFERRED EMBODIMENTS

The present invention particularly relates to:
13,14-didehydro-11-deoxy-11-hydroxymethyl-19-oxo-PGF₁α, and
13,14-didehydro-11-deoxy-11-hydroxymethyl-15(R)-19-oxo-PGF₁α.

I claim:

1. A compound of the formula

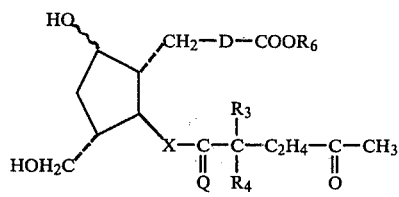

wherein D is
(1) $(CH_2)_3-(CH_2)_g-CH_2-$, or
(2) $(CH_2)_3-(CH_2)_g-CF_2-$;
wherein g is zero, one, two, or three;
wherein Q is α-OH:β-R₅ or α-R₅:β-OH, wherein R₅ is hydrogen or methyl;
wherein R₆ is
(a) hydrogen,
(b) alkyl of one to 12 carbon atoms, inclusive,
(c) cycloalkyl of 3 to 10 carbon atoms, inclusive,
(d) aralkyl of 7 to 12 carbon atoms, inclusive,
(e) phenyl,
(f) phenyl substituted with one, 2, or 3 chloro or alkyl groups of one to 3 carbon atoms, inclusive,
(g) $-(p-Ph)-CO-CH_3$,
(h) $-(p-Ph)-NH-CO-(p-Ph)-NH-CO-CH_3$,
(i) $-(p-Ph)-NH-CO-(p-Ph)$,
(j) $-(p-Ph)-NH-CO-CH_3$,
(k) $-(p-Ph)-NH-CO-NH_2$,
(l) $-(p-Ph)-CH=N-NH-CO-NH_2$,
(m) β-naphthyl,
(n) $-CH_2-CO-R_{28}$,
wherein (p-Ph) is para-phenyl or inter-para phenylene,
wherein R₂₈ is phenyl, p-bromophenyl, p-biphenylyl, p-nitrophenyl, p-benzamidophenyl, or 2-naphthyl, or
(o) a pharmacologically acceptable cation; wherein R₃ and R₄ are hydrogen, methyl, or fluoro, being the same or different, with the proviso that one of R₃ and R₄ is fluoro only when the other is hydrogen or fluoro; and
wherein X is $-C\equiv C-$.

2. A compound according to claim 1, wherein R₆ is hydrogen or methyl.

3. 13,14-Didehydro-11-deoxy-11-hydroxymethyl-19-oxo-PGF₁α, a compound according to claim 2.

4. 13,14-Didehydro-11-deoxy-11-hydroxymethyl-15(R)-19-oxo-PGF₁α, a compound according to claim 2.

* * * * *

UNITED STATES PATENT OFFICE
CERTIFICATE OF CORRECTION

Patent No. 4,296,246  Dated 20 October 1981

Inventor(s) John C. Sih

It is certified that error appears in the above-identified patent and that said Letters Patent are hereby corrected as shown below:

Column 2, line 5 and line 60, "-C=C-" should read -- -C≡C- --.

Signed and Sealed this

Ninth Day of February 1982

[SEAL]

Attest:

GERALD J. MOSSINGHOFF

Attesting Officer   Commissioner of Patents and Trademarks